(12) United States Patent
Kartalov et al.

(10) Patent No.: US 9,149,805 B2
(45) Date of Patent: Oct. 6, 2015

(54) MICROFLUIDIC FLUID SEPARATOR AND RELATED METHODS

(71) Applicants: UNIVERSITY OF SOUTHERN CALIFORNIA, Los Angeles, CA (US); APIC CORPORATION, Culver City, CA (US); CALIFORNIA INSTITUTE OF TECHNOLOGY, Pasadena, CA (US)

(72) Inventors: Emil P. Kartalov, Pasadena, CA (US); Axel Scherer, Woodstock, VT (US); Koichi Sayano, Montebello, CA (US)

(73) Assignees: UNIVERSITY OF SOUTHERN CALIFORNIA, Los Angeles, CA (US); APIC CORPORATION, Culver City, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 200 days.

(21) Appl. No.: 13/913,321

(22) Filed: Jun. 7, 2013

(65) Prior Publication Data

US 2013/0267005 A1  Oct. 10, 2013

Related U.S. Application Data

(62) Division of application No. 13/206,362, filed on Aug. 9, 2011, now Pat. No. 8,480,978.

(60) Provisional application No. 61/373,216, filed on Aug. 12, 2010.

(51) Int. Cl.
*B01L 3/02* (2006.01)
*B01L 3/00* (2006.01)
(Continued)

(52) U.S. Cl.
CPC ........ *B01L 3/502753* (2013.01); *A61M 1/3496* (2013.01); *A61M 1/3633* (2013.01);
(Continued)

(58) Field of Classification Search
CPC ........ B01D 24/06; B01D 24/14; B01D 24/22; B01D 25/00; B01D 25/003; B01D 25/04; B01D 27/14; B01D 27/146; B01D 27/148; B01D 46/0023; B01D 46/0024; B01D 46/005; B01D 2201/18; B01D 2201/82; B01D 2201/184; B01D 2201/188; B01L 3/502753; B01L 3/502761; B01L 3/502769; B01L 3/50255; B01L 2300/0681; B01L 2300/0816; B01L 2300/0864
USPC ......... 422/534–535, 422–423, 427–428, 551, 422/553–554; 210/321.6, 322; 436/174, 436/177–178
See application file for complete search history.

(56) References Cited

U.S. PATENT DOCUMENTS 5,034,124 A    7/1991  Kopf .............................. 210/231
5,256,294 A *  10/1993 van Reis ........................ 210/637
(Continued)

OTHER PUBLICATIONS

Notice of Allowance issued for U.S. Appl. No. 13/206,362 filed on Aug. 9, 2011 in the name of Emil Kartalov; mailing date: Apr. 1, 2013.
(Continued)

*Primary Examiner* — Brian R Gordon
(74) *Attorney, Agent, or Firm* — Steinfl & Bruno LLP (57) ABSTRACT

A microfluidic fluid separator for separating target components of a fluid by filtration is described. Methods for separating target components of a fluid by filtration and methods for processing blood on a large scale with the microfluidic fluid separator are provided.

17 Claims, 9 Drawing Sheets

(51) Int. Cl.
*A61M 1/36* (2006.01)
*A61M 1/34* (2006.01)

(52) U.S. Cl.
CPC ....... *A61M1/3472* (2013.01); *B01L 2300/0645* (2013.01); *B01L 2300/0681* (2013.01); *B01L 2300/087* (2013.01); *B01L 2300/0816* (2013.01); *B01L 2300/0864* (2013.01); *B01L 2400/0424* (2013.01); *Y10T 436/25125* (2015.01); *Y10T 436/25375* (2015.01)

(56) References Cited

U.S. PATENT DOCUMENTS

| | | | |
|---|---|---|---|
| 6,303,389 B1 | 10/2001 | Levin et al. | 436/518 |
| 6,866,783 B2 | 3/2005 | Baurmeister et al. | 210/649 |
| 7,041,510 B2 * | 5/2006 | Seul et al. | 436/518 |
| 7,153,421 B2 | 12/2006 | Koehler et al. | 210/198.2 |
| 7,390,676 B2 * | 6/2008 | Seul et al. | 436/518 |
| 7,520,988 B2 | 4/2009 | Pahl et al. | 210/321.6 |
| 7,939,034 B2 | 5/2011 | Shiraishi et al. | 422/513 |
| 8,084,274 B2 * | 12/2011 | Seul et al. | 436/518 |
| 8,262,909 B2 | 9/2012 | Angelescu et al. | 210/321.75 |
| 2003/0178358 A1 | 9/2003 | Osenar et al. | 210/321.75 |
| 2003/0213748 A1 | 11/2003 | Jangbarwala | 210/638 |
| 2004/0256318 A1 * | 12/2004 | Iida et al. | 210/634 |
| 2010/0284861 A1 | 11/2010 | Horiike | 422/70 |
| 2012/0298578 A1 * | 11/2012 | Herrington et al. | 210/636 |

OTHER PUBLICATIONS

Restriction Requirement issued for U.S. Appl. No. 13/206,362 filed on Aug. 9, 2011 in the name of Emil Kartalov; mailing date: Dec. 6, 2012.

* cited by examiner

MICROFLUIDIC FLUID SEPARATOR AND RELATED METHODS

CROSS REFERENCE TO RELATED APPLICATIONS

The present application is a divisional of U.S. patent application Ser. No. 13/206,362 filed on Aug. 9, 2011, now U.S. Pat. No. 8,480,978, which, in turn, claims priority to U.S. Provisional Application No. 61/373,216, filed on Aug. 12, 2010, all of which is incorporated herein by reference in its entirety.

STATEMENT OF GOVERNMENT GRANT

This invention was made with government support under EB007151 awarded by the National Institutes of Health. The government has certain rights in the invention.

FIELD

The present disclosure relates to microfluids. In particular, it relates to microfluidic fluid separators and related methods.

SUMMARY

According to a first aspect of the disclosure, a microfluidic filter chip for separating target components of a fluid by filtration is described, the target components adapted to exit though a plurality of output terminals of the microfluidic filter chip, the microfluidic filter chip comprising a plurality of filtering stages comprising stacked perforated surfaces, wherein: a flow channel is provided above and below any perforated surface, each perforated surface comprises a plurality of openings through which components of the fluid commensurate with the openings is adapted to pass, openings of a given perforated surface are smaller than openings of a previous perforated surface and larger than openings of a subsequent perforated surface, a fluid flow direction is parallel to a flow channel direction, an input of the microfluidic filter chip is provided at an entrance of an uppermost flow channel, and an output terminal of the microfluidic filter chip is provided at an end of any flow channel.

According to a second aspect of the disclosure, a microfluidic fluid separator for separating target components of a fluid by filtration is described, the target components configured to exit though a plurality of output terminals, the microfluidic fluid separator comprising: a horizontal filtering layer, wherein: the horizontal filtering layer comprises an input channel which is consecutively split in a first direction, into a plurality of input channels coupled to a plurality of microfluidic filter chips, each microfluidic filter chip comprises a plurality of filtering stages, each filtering stage of the plurality of filtering stages comprises stacked perforated surfaces, a flow channel is provided above and below any perforated surface, the plurality of microfluidic filter chips are coupled through a plurality of flow channels, the flow channels are in parallel along a second direction, and the parallel flow channel outputs are combined in the first direction.

According to a third aspect of the disclosure, a method for separating a fluid by filtration through a microfluidic filter chip is described, the fluid comprising a plurality of target components, the method comprising: providing the fluid to an input of a microfluidic filter chip, wherein the microfluidic filter chip comprises a plurality of flow channels, each flow channel being coupled with at least one other flow channel; directing the target components to corresponding flow channels based on size of the target components, thus separating the fluid.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

DETAILED DESCRIPTION

The term "microfluidic filter chip" as used herein is defined to mean a filter element comprising at one perforated surface that may be used in manipulation of fluids that are constrained to a small (e.g., less than 5 mm) diameter.

The term "microfluidic fluid separator" as used herein is defined to mean a device adapted to perform microfluidic filtering.

The term "blood components" as used herein is defined to mean any components that may be found in a sample of blood. For example, the blood components may include, but are not limited to, white blood cells (WBCs), red blood cells (RBCs), platelets, plasma, and bacteria.

The term "silicon-on-insulator wafer" as used herein is defined to mean a thin sheet comprising one or more layers of silicon dioxide and insulator.

The term "pore" as used herein is defined to mean any opening through which matter, commensurate with the opening, can pass.

The term "scrubbing" as used herein is defined to mean any method for removing or partially removing any undesired blood components from desired blood components. The undesired blood components may include, but are not limited to, bacteria. The desired blood components may include, but are not limited to, WBCs, RBCs, platelets, and plasma. For example, according to one embodiment, scrubbing refers to a process of collecting blood from a patient and then returning the blood to the patient after removal or partial removal of undesired blood components.

The term "molecular diagnostics" or "diagnostic testing" as used herein is defined to mean any medical or biological testing that may be performed on a biological sample for analytical or diagnostic purposes. For example, the biological sample may include, but is not limited to, a blood sample.

The term "dielectric separation" as used herein is defined to mean a method of separating different types of substances or cells based on a difference in charge that may be either inherent and/or induced. For example, a dielectric separation can include, but is not limited to, separation of large bacteria from WBCs, mid-sized bacteria from RBCs, and small bacteria from platelets.

The term "cross-flow filtration" as used herein is defined to mean a filtration in which a fluid flow direction is parallel to a filtering surface.

The term "dead-on filtration" as used herein is defined to mean a filtration in which a fluid flow direction is normal to a filtering surface.

The term "cross-flow filter" as used herein is defined to mean a filter that is used for cross-flow filtration.

The term "dead-on filter" as used herein is defined to mean a filter that is used for dead-on filtration.

The term "via" as used herein is defined to mean a vertical passage or opening. For example, a via in a silicon-on-insulator wafer can be fabricated using photolithography and etching.

The term "point-of-care" as used herein is defined to mean a location on or near a site of patient care where medical testing and/or treatment can be performed. For example, locations for point-of-care may include but is not limited to, hospitals, patient homes, a physician's office, or a site of an emergency.

Figure 1:
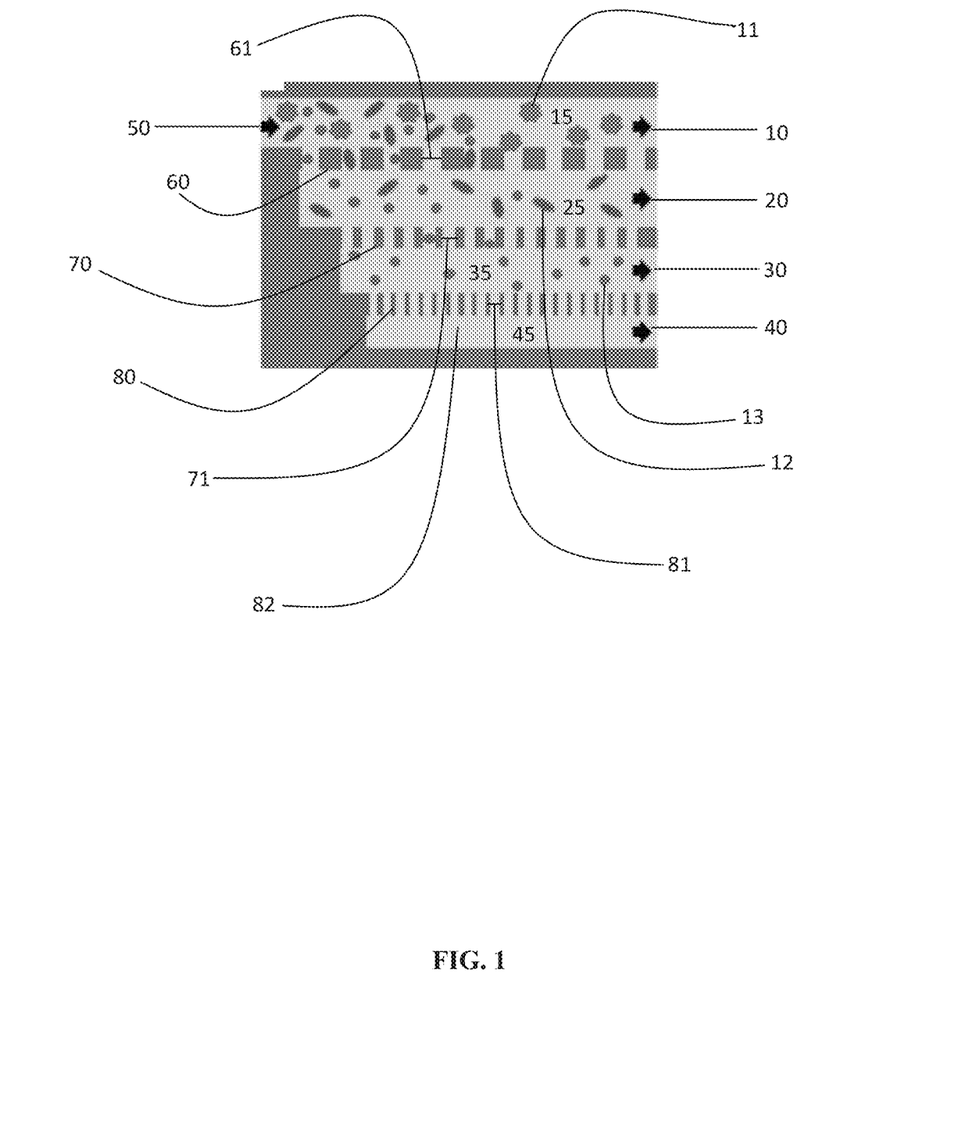
FIG. 1 shows a side-view schematic of a microfluidic filter chip according to some embodiments herein described.

In some embodiments, a microfluidic filter chip can be used to separate target components of a fluid. For example, the fluid may be blood and the target components, blood components. FIG. 1 shows a side-view schematic of an exemplary microfluidic filter chip. The microfluidic filter chip comprises vertically stacked perforated surfaces wherein flow channels are formed above and below any perforated surface. The perforated surfaces can have pores through which adjacent channels are coupled thereby creating different filtering stages. The perforated surfaces may include, but are not limited to silicon-on-insulator wafers; surfaces comprising polycarbonate or elastomer; and/or filtration materials.

Blood components that can be separated using the microfluidic filter chip may include, but are not limited to, white blood cells (11) (WBCs), red blood cells (12) (RBCs), platelets (13), and plasma (82). Separation of blood components is typically based on size of the blood components and can be achieved by stacking porous surfaces of varying pore size configured for various cell sizes. For example, the porous surface may comprise an SOI wafer (see, for example, FIG. 5).

It should be noted that while separation of blood cells is described here by way of example, a separation is in no way limited to blood cells. For example, a microfluidic filter chip can be adapted to separate other mixtures of cells, wherein the cells differ in size.

Human RBCs are disks of diameter 6-8 microns and thickness 2 microns and have an occurrence of approximately 5 million cells per µL of blood. Human WBCs, comprising mostly neutrophils (approximately 60%, 10-12 micron diameter) and lymphocytes (~30%, 7-8 microns diameter) have a total occurrence of about 4,000-11,000 cells per µL of blood. Human platelets (thrombocytes) are 2-3 micron diameter and have an occurrence of 150,000-400,000 cells per µL of blood.

As RBCs can squeeze through openings smaller than 6 microns by deformation [see ref 4] these relative sizes can be used to perform a physical separation. For example, a set of openings of size 5 microns may not allow WBCs to pass, but may allow deformable RBCs and platelets to pass. A set of 2-3 micron openings may allow platelets to pass but may not allow most of the RBCs to pass. The resulting distributions are typically governed by statistics, with respective means allowing separation of components by physical size.

A blood sample can enter the microfluidic filter chip at an input (50) and flow horizontally, similar to a cross-flow filtration system [see refs 1-3].

As shown in FIG. 1, the microfluidic filter chip may comprise several different filtering stages (60, 70, 80). With each subsequent filtering stage (60, 70, 80), the pores in the microfluidic filter chip get progressively smaller from a top-most stage (60) to a bottom-most stage (80). For example, a first pore diameter $d_1$ (61) of an initial filtering stage (60) can be configured for retaining WBCs (11), a second pore diameter $d_2$ (71) can be used for a second filtering stage (70) and configured for retaining RBCs (12), and a third pore diameter $d_3$ (81) can be used for a third filtering stage (80) and configured for retaining platelets (13), thus allowing plasma (82) to pass.

While the orientation of the embodiments as seen FIGS. 1-4 may be a preferred orientation in order to exploit hydrostatic pressure, it should be noted that this these embodiments are in no way limited to this orientation and can be adapted to function in any orientation. For example, a filtration driven by a mechanical source of pressure such as the methods described above, would be capable of separating components of a fluid as previously described, regardless of its orientation with respect to the vector of gravity. Therefore, the so-called "top-most", "bottom-most", "horizontal", "vertical", "above", "below", "left", "right", "downward", "upward", "higher", "lower", etc. as used herein are only used for convenience of expression and visualization with the provided schematic representations.

Passage of a blood sample through the microfluidic filter chip is now described. After the blood sample enters the microfluidic filter chip at input (50), the blood sample can flow horizontally from left to right through a first flow channel (15), as shown in FIG. 1. As the blood sample continues along the horizontal axis, blood components that are not able to fit through a first set of pores (see, for example, (61)) will continue to travel across the first flow channel (15) and exit through an output terminal (10).

Blood components that are able to fit through the first set of pores (61) may travel down to a second flow channel (25) and continue to flow horizontally. Blood components that are not able to fit through a second set of pores (see, for example, (71)) will continue to travel across the second flow channel (25) and exit through output terminal (20).

Blood components in the second flow channel (25) that are able to fit through the second set of pores (71) may travel down to a third flow channel (35) and continue to flow horizontally. Blood components that are not able to fit through a third set of pores (see, for example, (81)) will continue to travel across the third flow channel (35) and exit through output terminal (30).

Any components in the third flow channel (35) that are able to fit through the third set of pores (see, for example, (81)) may travel down to a fourth flow channel (45) and continue to flow horizontally, ultimately exiting through output terminal (40). FIG. 1 is a cross-section of a larger device shown in top-view in FIG. 2. (see cross-section (290)), FIG. 2). It should be noted that, although FIG. 1 shows three filtering stages (60, 70, 80), more filtering stages or less filtering stages may be used.

While it is possible that a fraction of a particular component that is adapted to pass through a set of pores, continues traveling horizontally without passing through said pores, the number of pores and the length of the horizontal channels compared to the size of the cells, minimizes this fraction. For example, a few RBCs may remain in channel 15 and exit into output 10, but the vast majority will exit through 20.

Figure 2:
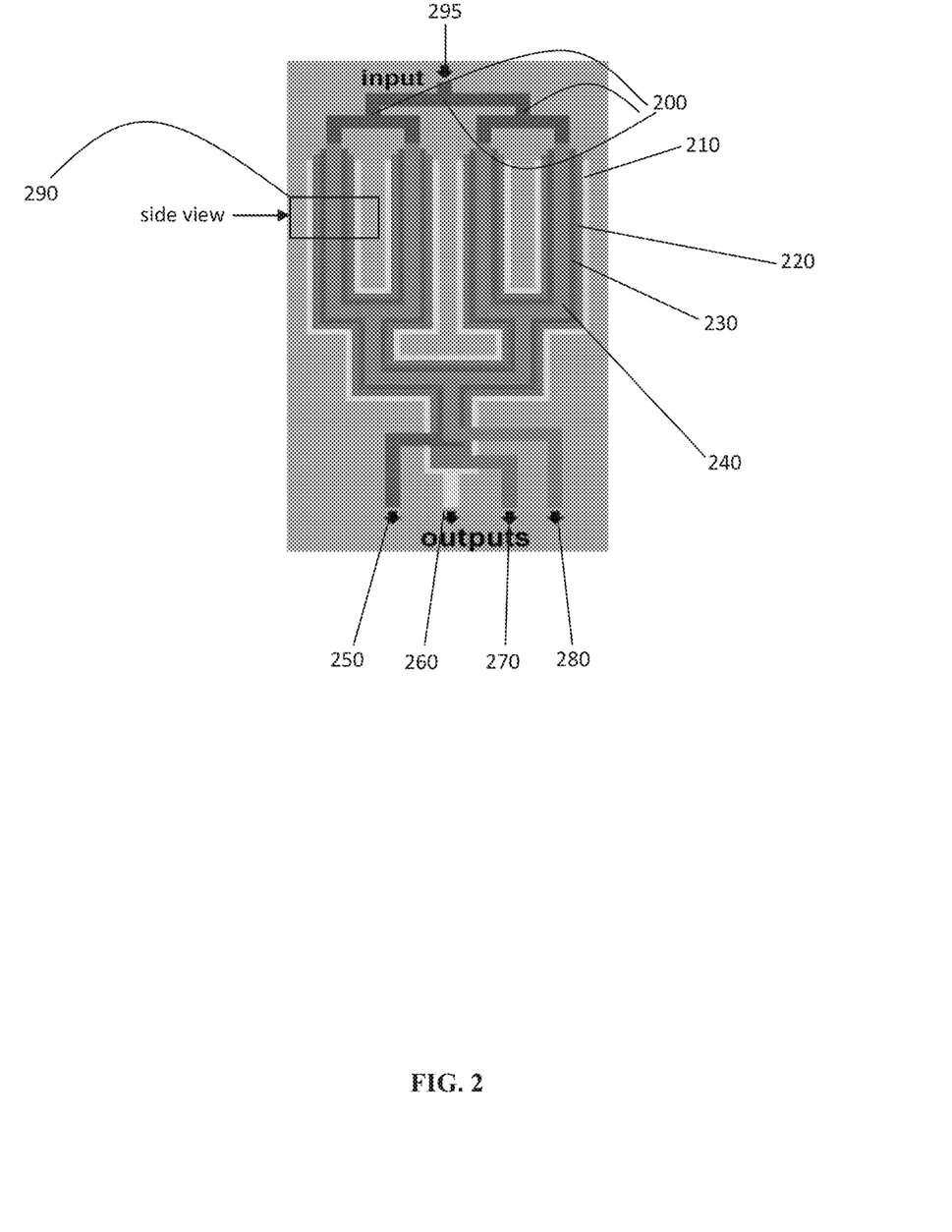
FIG. 2 shows a top-view schematic of a microfluidic fluid separator according to some embodiments herein described.

FIG. 2 shows a top-view schematic of a microfluidic fluid separator. In some embodiments, the microfluidic fluid separator can be employed for the separation of major blood components according to FIG. 2. A vertical cross-section (290) of the microfluidic fluid separator can be, for example, the microfluidic filter chip as shown in FIG. 1.

FIG. 2 shows a schematic of the microfluidic fluid separator that can be obtained by running flow channels (210-240) in parallel to increase throughput and reduce clogging.

In accordance with the embodiment shown in FIG. 2, flow channels (210-240) are consecutively bifurcated to give a base-2 geometric progression of parallel branching. In FIG. 2, an input channel (295) is shown with 2 splits (200) for simplicity, thus providing four parallel flow channels, but can be split n times to provide $2^{(n-1)}$ parallel flow channels with equal flow path length. Such geometric progression involves a small number of splitting stages to build a large parallel array. This large parallel array can generally be implemented to allow utilized surface area of the microfluidic filter chip to approach that of device area.

It should be noted that while the input channels are shown to be split by consecutive bifurcation with a base-2 geometric progression, the input channels can be split in any fashion.

After a flow channel path length that is configured to give pure blood components, the flow channels (210-240) are reunited analogously to the manner in which the flow channels (210-240) are branched to give singular output terminals (250-280) for each flow channel (210-240) for convenience.

A typical flow channel path length is determined primarily by size of the perforated surfaces. For example when the perforated surface is an SOI wafer, a 3 inch SOI wafer may have a central usable area of roughly 5×5 cm, which can allow the parallel flow channels to approach 5 cm in length. A 5 inch SOI wafer may have 8×8 cm central usable area, which can allow the parallel flow channels to approach 8 cm in length. However, it is possible to have a flow channel path length that spans the entire length of the SOI wafer.

In FIG. 2, progressive widening of the flow channels (210-240) can be seen, with a WBC flow channel (240) being the narrowest, followed by a RBC flow channel (250), a platelet flow channel (220), and a plasma flow channel (210) being the widest. Accordingly, the WBCs exit through output terminal (280), the RBCs through output terminal (250), the platelets through output terminal (270), and the plasma through output terminal (260).

A microfluidic fluid separator as described in FIG. 2 can have an output that is approximately 3,000 times that of conventional devices [see refs 4-5] due to the parallel arraying. A microfluidic fluid separator as described in FIG. 2 can thus have an output of around 14 L/hr.

Figure 3:
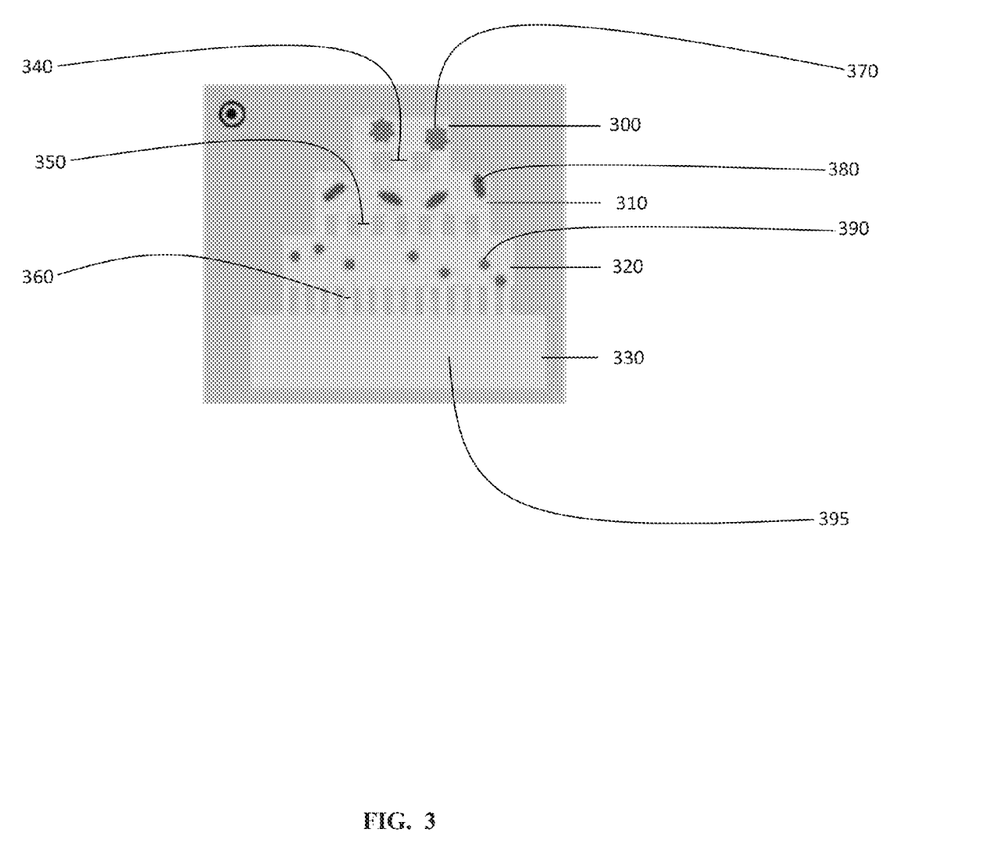
FIG. 3 shows a rear-view schematic of a microfluidic filter chip according to some embodiments herein described.

FIG. 3 shows a schematic of a microfluidic filter chip, such as the microfluidic filter chip shown in FIG. 1, this time from a rear-view perspective. FIG. 3 indicates a progressive widening and deepening of the flow channels (300-330) and a progressive decrease in pore size (340-360) from top to bottom of the microfluidic filter chip (from 300 to 330).

WBCs (370) remain in a first flow channel (300), which is narrower and shallower than any subsequent flow channel (310-330). RBCs (380) and other matter of similar or smaller size continue down to a lower (relative to (300)) flow channel (310), which is narrower and shallower than any subsequent flow channel (320-330) and wider and deeper than any previous flow channel (300). Platelets (390) and other matter of similar or smaller size can continue down to a lower (relative to (310)) flow channel (320), which is narrower and shallower than any subsequent flow channel (330) and wider and deeper than any previous flow channel (300-310). Plasma (395) may continue down to a lower (relative to (320)) flow channel (330), which is wider and deeper than any previous flow channel (300-320).

Increasing depths of the fluid flow channels of FIG. 3 may be considered a further sophistication with respect to increasing widths of the fluid flow channels of FIG. 1. Such architectures of FIGS. 2 and 3 can provide a fluidic conductivity bias towards lower filtration stages to aid in a fluid component separation.

For example, Poiseuille's law indicates that in viscous flow, a fluidic current (or throughput) is proportional to the third power of a small cross-sectional dimension and to the first power of a large cross-sectional dimension. Therefore, having subsequent flow channels, which are wider and deeper than previous flow channels, can increase throughput and conductivity of the flow channels. On the other hand, because each channel may be coupled in parallel with a neighboring channel, when their conductivity is higher, flow may split with preference to higher conductivity pathways.

Thus the architecture of FIGS. 1 and 3 can enable fluidic conductivity bias towards lower flow channels. It should be noted that the strength of the bias, i.e. the ratios of conductivity, can be tuned by adjusting the depth and width of each flow channel. Such tuning allows for optimization of the flow distribution and fluid component separation efficiency.

The extremes of such tuning can be a high bias downward, which may lead to clogging, as the device may begin to act as a dead-on filter rather than a cross-flow filter; little to no bias either way, which may make separation of the fluid components inefficient and of lower purity; and very high bias upward (i.e. highest conductivity in a topmost channel), which may impede the separation of fluid components almost completely.

The flow of blood and/or a fluid in a microfluidic filter chip as depicted in FIG. 3 occurs in a direction perpendicular to the plane of the paper.

Figure 4:
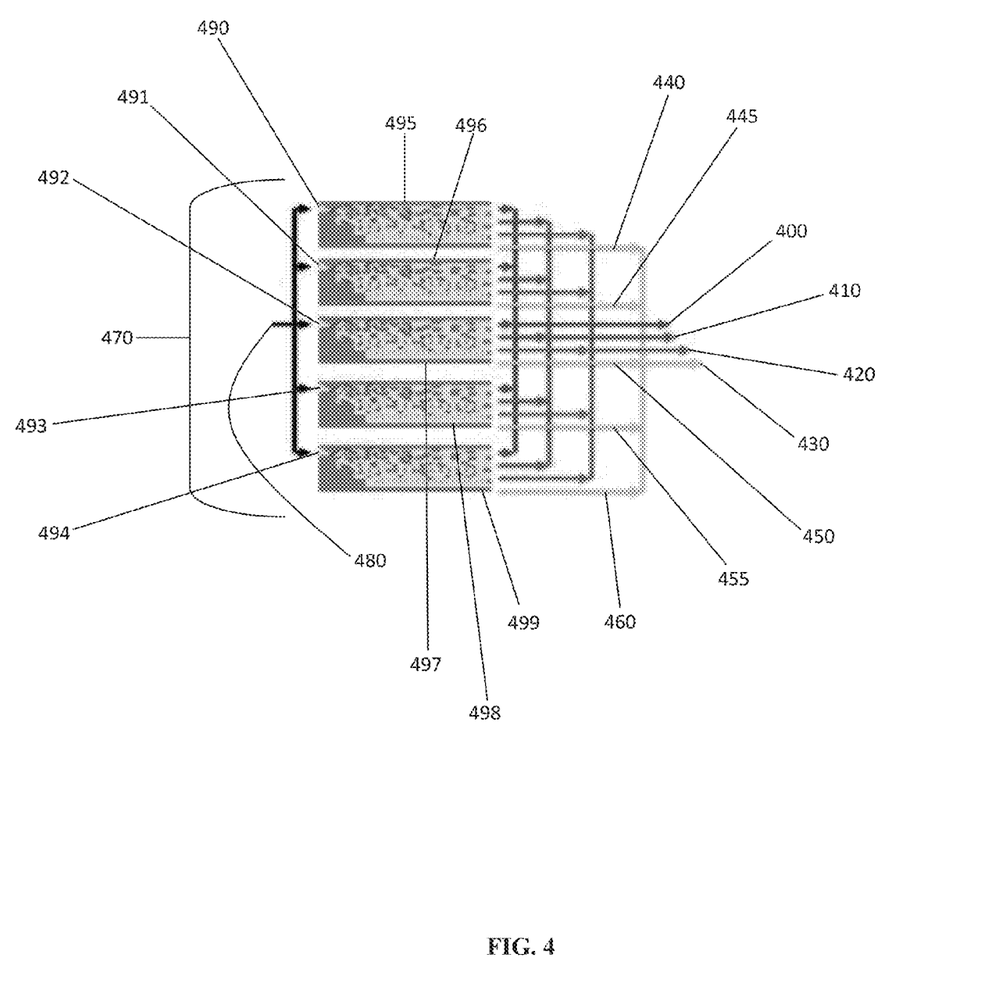
FIG. 4 shows a side-view schematic of a paralleled filtering device according to some embodiments herein described.

In some embodiments, a vertically arrayed configuration of a microfluidic fluid separator can be constructed, for example, according to the embodiment of FIG. 4, which shows a side-view schematic of such a vertical arraying (470). FIG. 4 details a vertical arraying (470) of the devices described, for instance, in FIG. 1 and FIG. 2. It should be noted that a vertical arraying of FIG. 1 is shown in FIG. 4 for simplicity and that the use of such vertical arraying is not limited to this embodiment or to the embodiments shown in FIG. 1 and FIG. 2.

The vertical arraying (470) can be used to maximize processing volume and throughput. The vertical arraying (470) can be achieved by stacking (495-499) the paralleled microfluidic fluid separator of FIG. 2 and splitting an initial input (480) vertically through the stacked filtering layers (495-499) to yield individual inputs (490-494) for each stacked microfluidic filter chip (495-499). FIG. 4 shows five stacks (495-499). More or fewer stacks can also be used.

For example, starting with a single input (480), this input can subsequently split into a plurality of additional inputs (490-494). These additional inputs (490-494) may then individually enter a plurality of microfluidic filter chips (495-499), for example, as described in FIG. 1, that are stacked in the vertical direction. The output terminals can then reunite to give single output terminals for each analogous flow channel (400-430). For example, output terminals for a plasma flow channel (440-460) can unite to form a single plasma flow channel output terminal (430).

Each layer of microfluidic filter chips (495-499) in a stack can function independently from other layers, and their throughputs may thus be additive. Such vertical arraying (470) can affect processing volume because each microfluidic filter chip (495-499) is thin (approximately 0.5 mm) and utilization of, for instance, over 100 layers in a stack with each layer being approximately 0.5 mm still yields a portable paralleled filtering device approximately 50 mm in height, well-suited for point-of-care testing.

It is important to note that direction of arraying is in no way limited to the vertical direction. For example, the filtering layers may be arrayed vertically, horizonally, both vertically and horizontally, or other direction(s). The result would be the same for any direction of arraying the filtering layers—filtering layers in parallel will give effective throughput and processivity that are the sum of the throughputs and processivities the individual filtering layers.

A separation of a fluid using a microfluidic fluid separator can be performed using hydrostatic pressure as each meter of relative elevation will produce ~0.1 atm or ~1.5 psi of driving pressure, while the fluidic resistance in a highly parallelized microfluidic fluid separator such as those in FIGS. 2 and 4, will be relatively small. For example, hydrostatic pressure may be utilized by elevating the starting sample container with respect to the microfluidic filter chip similar to the manner of intra-venous (IV) feeds in hospitals, although there are other ways to exploit hydrostatic pressure for this purpose.

The use of hydrostatic pressure can be advantageous due to its ease of use; however, mechanical sources of pressure may also be used, including but not limited to a manually operated piston such as a syringe or a pump. For example, the pumps may be electroosmotic, mechanical, and/or peristaltic pumps.

A microfluidic filter chip according the embodiments in FIG. 1 and FIG. 3, employing an SOI wafer as a perforated surface, utilizes a filtering surface area which approaches the surface area of the microfluidic filter chip. According to some embodiments, a microfluidic filtering chip can be roughly 900 mm$^2$ (30 mm×30 mm). This 900 mm$^2$ utilized surface area comprising nearly the entire microfluidic filter chip surface area, in contrast to previously described microfluidic filter chips [see ref 4-5] which utilize a surface area of 0.3 mm$^2$ (a thin sliver perpendicular to two microfluidic filter chips, each of the two chips having a surface area 30 mm×5 μm), indicates roughly a factor of 3,000 times more utilized surface area in the present case.

A larger wafer can also be used, for example, a 90 mm×90 mm wafer, which would utilize 27,000 times more surface area.

Moreover, integration of vertical arraying according to the embodiment of FIG. 4 into a microfluidic fluid separator such as the one in FIG. 2 by implementing a stack of 100 vertical layers can give an output which is 100 times the output without stacking, thus giving roughly 300,000 times the output (30 mm×30 mm wafers) or 2,700,000 times the output (90 mm×90 mm wafer) of previously described devices [see ref 4-5].

These calculations are given as examples of the outputs of various embodiments and the numbers may vary.

For example, a microfluidic fluid separator according to FIG. 2, with arraying such as that depicted in FIG. 4, may be used in medical applications to filter human blood samples. At an exemplary rate of 70 L/hr of blood, such a device can perform 14 complete cycles of scrubbing in 1 hr, considering that an adult human has approximately 5 L of blood.

Figure 5:
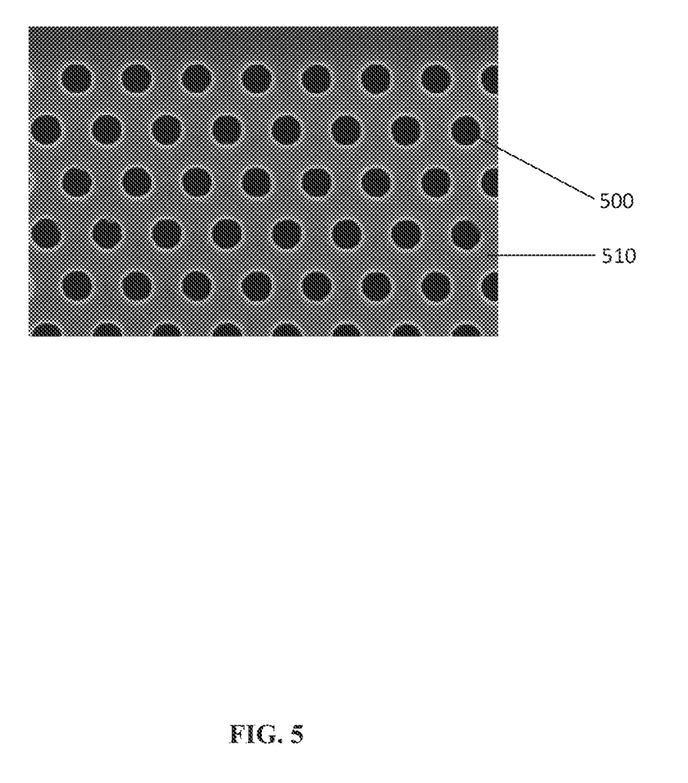
FIG. 5 shows a top-view of a silicon-on-insulator wafer (SOI) according to some embodiments herein described.

In some embodiments, a microfluidic filter chip, as seen for example in FIGS. 1 and 3, comprises a silicon-on-insulator (SOI) wafer, such as the one in FIG. 5. The SOI wafer (510) can be fabricated to have defined filtration pores (500). An SOI wafer such as the one in FIG. 5 can withstand normal sterilization temperatures, for example between 100-134° C., and may be disposable so that cross-contamination of blood samples can be avoided.

Figure 6:
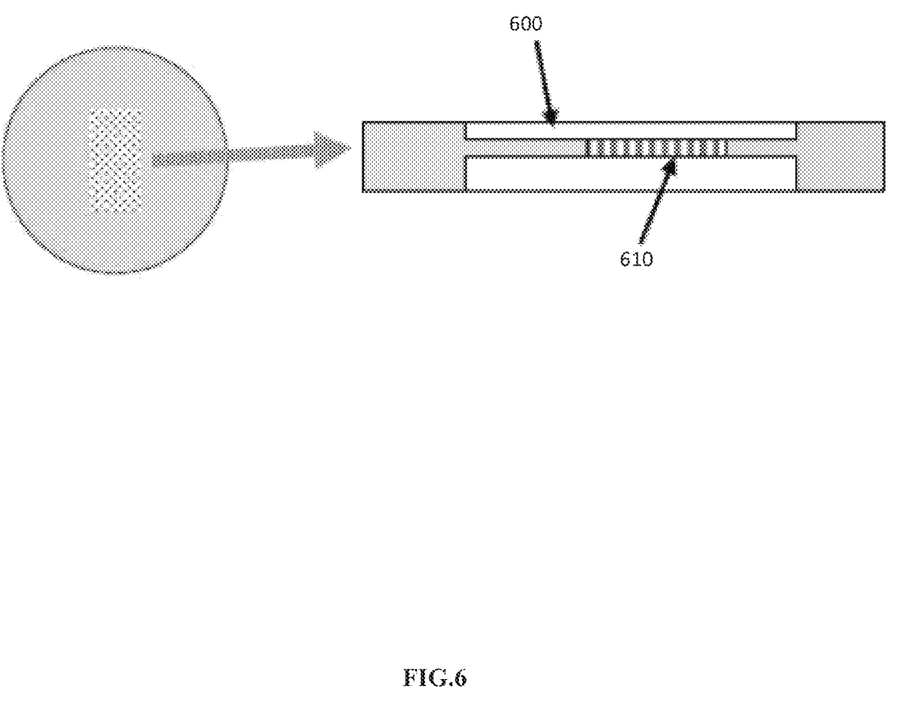
FIG. 6 shows a depiction of a vias fabrication according to some embodiments herein described.

In some embodiments, vias (610) such as those shown in FIG. 6 may be used as filter apertures in an SOI wafer analogous to the pores as seen in FIG. 5.

Figure 7:
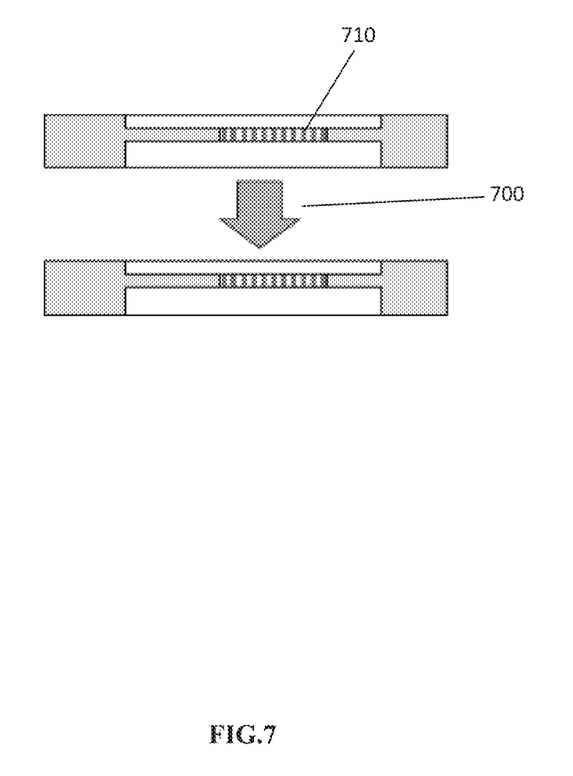
FIG. 7 shows a schematic of SOI wafer-to-wafer bonding according to some embodiments herein described.

In some embodiments, wafer-to-wafer bonding is utilized as shown in FIG. 7. Wafer to wafer bonding permits construction of multi-layer flow channels used to implement the parallelism (FIG. 2) of the microfluidic filter flow channels (FIG. 1-4). (700) indicates wafer to wafer bonding connected by vias (710).

In some embodiments, a microfluidic filter chip such as those seen in FIGS. 1 and 3 and/or a microfluidic fluid separator such as those depicted in FIGS. 2 and 4, can be adapted to separate biological molecules. The biological molecules may include, but are not limited to proteins, enzymes, peptides comprising natural and/or unnatural amino acids, natural or synthetic DNA or fragments thereof, and natural or synthetic RNA or fragments thereof. For example, a separation of two or more biological molecules can be based on relative size of the biological molecules. As with separation of blood components, the efficiency of separation of biological molecules can be tuned at least by adjusting pore size of the perforated surface, flow channel length, flow channel depth, and/or flow channel width.

In some embodiments, microfluidic filter chips and/or microfluidic fluid separators such as those described in FIGS. 1-4 can be used for separation and purification of blood components applied for medical applications.

Figure 8:
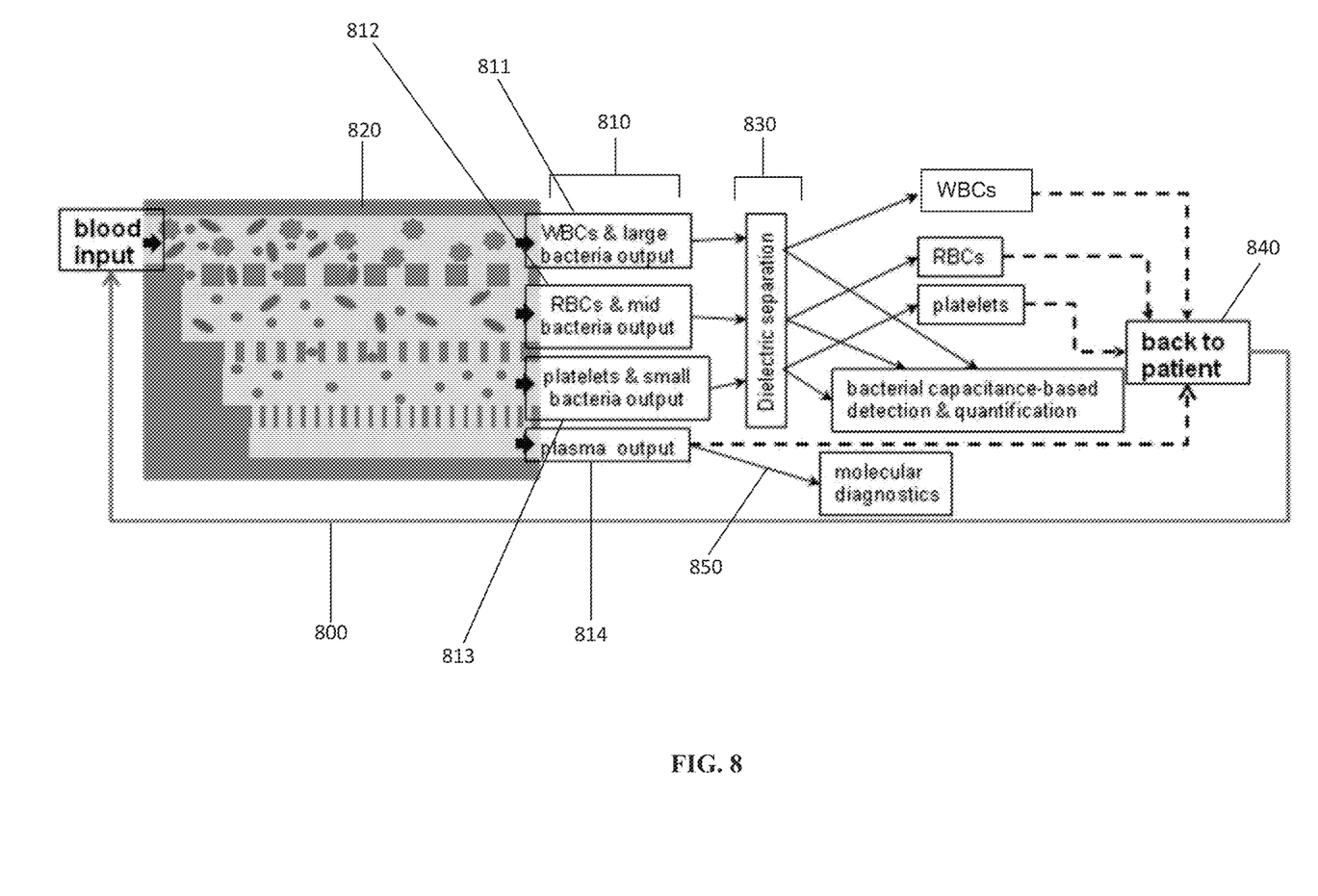
FIG. 8 shows a schematic of an application of a microfluidic fluid separator for blood separation and purification for medical purposes according to some embodiments herein described.

FIG. 8 shows a schematic of an exemplary medical application. Blood may be obtained directly from a patient (800), purified by an initial separation of blood components (810), and returned to the patient (840) after a dielectric separation of bacteria (830) from blood components in the microfluidic filter chip (820) and/or molecular diagnostics (850). For example, an initial separation of major blood components may include but is not limited to, a separation of WBCs and large bacteria (811), RBCS and mid-sized bacteria (812), platelets and small bacteria (813), and plasma (814). Each cellular bin (811-814) may then further be processed, returned to a patient, or discarded.

Dielectric separation is based on the known phenomenon that different cells can have different dielectric properties. For example, RBCs do not have nuclei and thus do not have genomic DNA, which makes them less susceptible to dielectric interactions. By comparison, bacteria have DNA, so they can be oriented by application of electrical fields. For example, if electric fields are applied perpendicularly to the channel, the bacteria would orient perpendicular to the channel as well, which will increase their drag and thus produce a method of fluidic discrimination.

In some embodiments, other known methods can be incorporated to separate blood components from a corresponding bacteria contaminant including, the use of conjugated magnetic nanoparticles as tags for the bacteria, in combination with magnetic fields applied across the channel, to trap and remove bacteria from the fluid flow. Additionally, known methods for removing blood contaminants other than bacteria may be used in conjunction with a microfluidic fluid separator.

Figure 9:
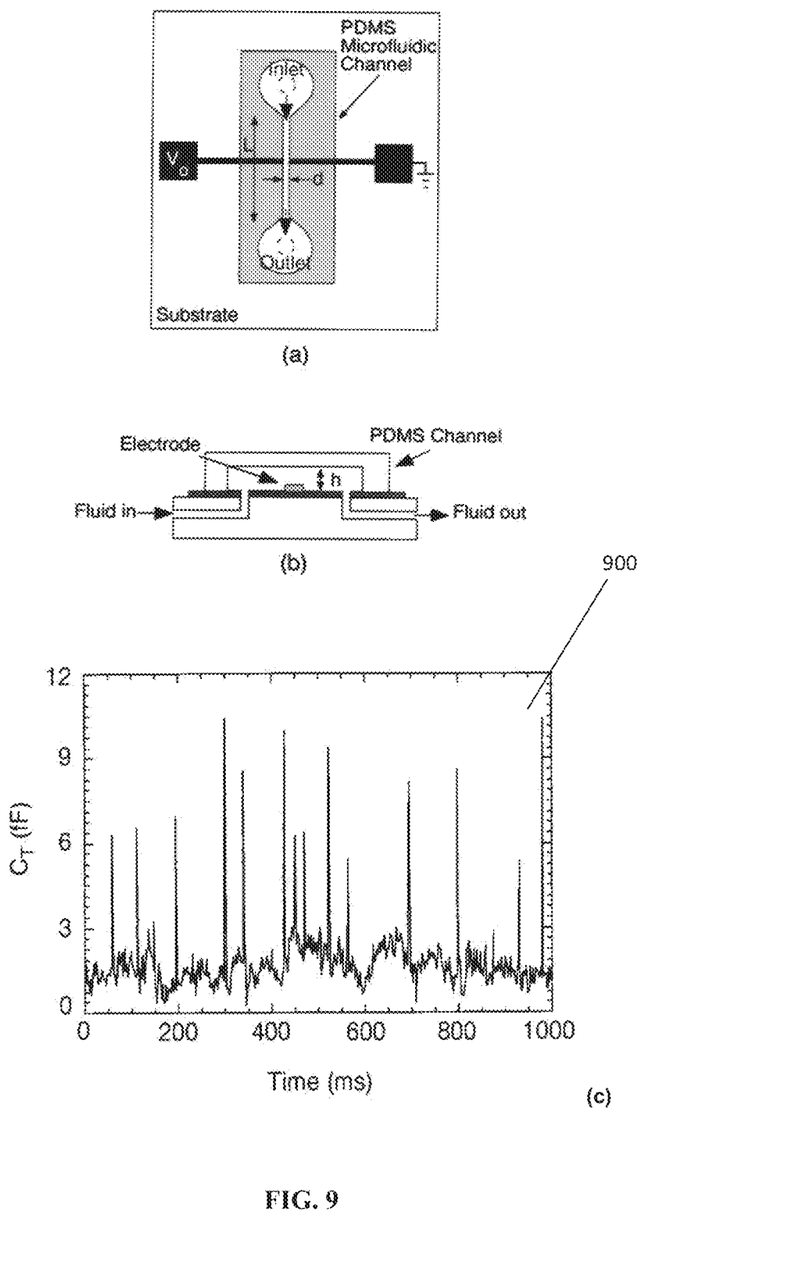
FIG. 9 shows a schematic of a cell sensing technique that can be used in conjunction with a microfluidic fluid separator, such as the one in FIG. 8.

In some embodiments, a cell sensing technique as depicted in (900), which measures capacitance as a function of time, can be used in conjunction with a filtering device according to FIG. 9 to detect and/or quantify different types of cells. Known cell sensing techniques [see ref 6] may be used to detect the presence of a single cell by a capacitance change (c) that can be measured by electrodes (b) across a PDMS (polydimethylsiloxane) flow channel (a).

A capacitance-based detector such as the one depicted in (900) may be used in conjunction with a microfluidic fluid separator (FIGS. 2 and 4) in at least two different ways. For example, the capacitance-based cell detector may measure capacitance upon the fluid components exiting the microfluidic fluid separator or the capacitance-based detector can be integrated into the microfluidic fluid separator to measure capacitance concurrently with the separation of the fluid components.

Additional detection methods may also be utilized in conjunction with the microfluidic fluid separator and may include, but are not limited to optical detection, for example, by measuring refractive index, fluorescence detection, for example, with pathogen-specific labeling, and labeling with nanoparticles, the nanoparticles being detectable by optical or electromagnetic measurements.

In some embodiments blood can be scrubbed while simultaneously measuring bacterial load. For example, this can be done by performing capacitance measurements across exhaust channels that contain removed bacteria. A change of capacitance can correlate with the number of bacteria in the exhaust channel, from which calibration curves can be generated and used for quantification. This embodiment is exemplary of a microfluidic fluid separator with micro-scale precision coupled with macro-scale processing capability.

In some embodiments, a microfluidic fluid separator can process upwards of 5 L in approximately 15 min with the microfluidic fluid separator being roughly 50 mm in size. A microfluidic fluid separator with such features is well-suited for processing blood for medical purposes, particularly in point-of-care settings. Blood processing procedures may include but are not limited to, a separation of blood components, diagnostic testing of blood components, scrubbing, apheresis, dialysis, blood salvaging, and blood purification.

Apheresis, is a procedure wherein blood from a donor patient is separated into blood components in which at least one of the blood components is stored or donated to a receiving patient, and in which at least one of the blood components is returned to the donor patient.

For example, a method for performing apheresis may comprise connecting a donor patient to an input (295 or 480) of a microfluidic fluid separator as depicted in FIG. 2 or 4, drawing the donor patient's blood into the microfluidic fluid separator, allowing the blood to flow through the microfluidic fluid separator and exit through the outputs (250-280 or 400-430) to yield separated blood components, storing at least one of the blood components and/or donating the at least one blood component to a receiving patient, and returning at least one of the blood components to the donor patient.

The microfluidic fluid separator as in FIG. 2 or 4 would be capable of meeting the processing requirements of state of the art blood processing procedures as a typical processing volume for apheresis, for example, is approximately 5 L in 2 hrs. Thus, the microfluidic fluid separator having the ability to perform macro-scale processing with micro-scale precision can be utilized in various modes of operation. Methods for processing blood by using the microfluidic fluid separator in various modes of operation are now described.

A method for processing blood by operating the microfluidic fluid separator (FIG. 2 or 4) in a discrete diagnostic mode may comprise drawing blood from a donor patient into the microfluidic fluid separator, allowing the blood sample to flow through the microfluidic fluid separator and exit through outputs (250-280 or 400-430) to yield separated blood components, followed by performing diagnostic tests on the blood components. It should be noted, however, that the diagnostic tests can also be performed concurrently with the separation of the blood components. This method may further comprise storing the blood components and/or using the blood components for other purposes.

A method for processing blood by operating the microfluidic fluid separator (FIG. 2 or 4) in a discrete therapeutic mode may comprise drawing blood from a donor patient into the microfluidic fluid separator, allowing the sample to flow through the microfluidic fluid separator and exit through the outputs (250-280 or 400-430) to yield separated blood components on which a separation from contaminants may be performed. For example, a separation from contaminants may be a dielectric separation from bacteria. The method may further comprise storing the blood components for a period of time, and returning the blood components to the donor patient or to a receiving patient after the period of time.

The method for processing blood by operating the microfluidic fluid separator (FIG. 2 or 4) in discrete therapeutic mode, for example, may be applied to a method for performing blood salvaging. Blood salvaging is a process for purifying leaked blood from a patient during surgery so that the blood may be returned to the patient.

A method for performing blood salvaging by operating the microfluidic fluid separator (FIG. 2 or 4) in discrete therapeutic mode may comprise directing leaked blood from a patient into the input of the microfluidic fluid separator, allowing the blood to flow through the microfluidic fluid separator and exit through the outputs (250-280 or 400-430) as separated blood components, and returning at least one of the blood components to the patient, in which the method may comprise a further separation of the separated blood components from bacteria or other contaminants prior to returning the at least one of the blood components to the patient.

A method for processing blood by operating the microfluidic fluid separator (FIG. 2 or 4) in a continuous therapeutic mode may comprise drawing blood out of a patient and into the microfluidic fluid separator, allowing the blood to flow through the microfluidic fluid separator and exit through the outputs (250-280 or 400-430) as separated blood components, performing a purification(s) on the separated blood components comprising separating the blood components from bacteria or other contaminants to yield purified blood components, and returning all or portions of the purified blood components to the patient in a continuous cycle.

A method for processing blood by operating the microfluidic fluid separator (FIG. 2 or 4) in continuous therapeutic mode, for example, may be applied in a method to perform dialysis. A method for performing the dialysis may comprise directly connecting a patient to the input (295 or 480) of the microfluidic fluid separator, allowing the blood to flow through the microfluidic fluid separator and exit through the outputs (250-280 or 400-430) as separated blood components, performing a purification(s) on the separated blood components comprising separating the blood components from bacteria or other contaminants to yield purified blood components, and returning all or portions of the purified blood components to the patient in a continuous cycle until a desired level of purity is achieved.

A method for processing blood by operating the microfluidic fluid separator (FIG. 2 or 4) in a continuous therapeutic and diagnostic mode may comprise drawing blood out of a patient and into the microfluidic fluid separator, allowing the blood to flow through the microfluidic fluid separator and exit through the outputs (250-280 or 400-430) as separated blood components, performing diagnostic testing on the separated blood components either during flow of the blood components through the microfluidic fluid separator and/or upon the blood components exiting the microfluidic fluid separator, performing a purification(s) comprising separating the blood components from bacteria or other contaminants and, returning all or portions of the purified blood components to the patient in a continuous cycle.

The examples set forth above are provided to give those of ordinary skill in the art a complete disclosure and description of how to make and use the embodiments of the microfluidic fluid separator of the disclosure, and are not intended to limit the scope of what the inventors regard as their disclosure. Modifications of the above-described modes for carrying out the disclosure can be used by persons of skill in the art, and are intended to be within the scope of the following claims.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

LIST OF REFERENCES

1. Belfort, G., Davis, R. H., and Zydney, A. L. J. Membr. Sci. 96, 1-58 (1994).
2. Mielnik, M. M., Ekatpure, R. P., Saetran, L. R., Schonfeld, F. Lab Chip 5, 897-903 (2005).
3. Crowley, T. A., Pizziconi, V. Lab Chip 5, 922-929 (2005).
4. VanDelinder, V., Groisman, A. Anal. Chem. 78, 3765-3771 (2006).
5. Fan, R., Vermesh, O., Srivastava, A., Yen, B. K. H., Qin, L., Ahmad, H., Kwong, G. Liu, C. C., Gould, J., Hood, L., Heath, J. R. Nat. Biotechnol. 26:12, 1373-1378 (2008).
6. Sohn, L. L., Saleh, O. A., Facer, G. R., Beavis, A. J., Proc. Nat. Acad. Sci., 97, 10687-10690 (2000).

What is claimed is:

1. An array of microfluidic filter chips comprising a plurality of microfluidic filter chips, each microfluidic filter chip for separating target components of a fluid by filtration, the target components adapted to exit though a plurality of output terminals of the microfluidic filter chip, the microfluidic filter chip comprising:

a plurality of filtering stages comprising a stack of perforated surfaces including a top perforated surface and a bottom perforated surface, wherein:

a flow channel is provided above and below each perforated surface, each perforated surface comprises a plurality of openings through which components of the fluid commensurate with the openings are adapted to pass, the diameter of the openings in the perforated surfaces decreases sequentially from the top perforated surface to the bottom perforated surface, such that the diameter of the openings of the top perforated surface is larger than the diameter of the openings of all other perforated surfaces in the stack, an input of the microfluidic filter chip is provided at an entrance of the uppermost flow channel, an output terminal of the microfluidic filter chip is provided at an end of each flow channel, and for each stacked perforated surface, the flow channel above the stacked perforated surface is narrower and shallower than the flow channel below the stacked perforated surface, wherein the plurality of microfluidic filter chips is stacked and a corresponding output terminal of a flow channel of each microfluidic filter chip of the array corresponding to a same filtered particle size range for the microfluidic filter chips of the array is joined together with corresponding output terminals of the microfluidic filter chips of the array.

2. The array of microfluidic filter chips of claim 1, wherein the array is portable.

3. The array of microfluidic filter chips of claim 1, further comprising:
at least one electrode adapted to apply an electric field to the microfluidic filter chip.

4. The array of microfluidic filter chips according to claim 1, wherein the perforated surface comprises polycarbonate, elastomer, or silicon on insulator wafers.

5. A method for separating a fluid by filtration through the array of microfluidic filter chips according to claim 1, the fluid comprising a plurality of target components, the method comprising:
providing the fluid to the input of the array of microfluidic filter chips; and
directing the target components to corresponding flow channels based on size of the target components, thus separating the fluid.

6. The method according to claim 5, wherein the plurality of target components are cells, wherein the cells differ in size.

7. The method according to claim 5, wherein the plurality of target components are biological molecules.

8. The method according to claim 5, wherein the fluid sample comprises at least one of a protein, a peptide comprising natural and/or unnatural amino acids, an enzyme, natural or synthetic DNA or fragments thereof, and natural or synthetic RNA or fragments thereof.

9. The method according to claim 5, wherein the fluid is a sample of bodily fluid.

10. The method according to claim 9, wherein the bodily fluid is a blood and the fluid components are blood components.

11. The method according to claim 10, wherein the blood components comprise at least one of WBCs, RBCS, platelets, and plasma.

12. The method of claim 5, further comprising:
applying an electric field to the microfluidic filter chip.

13. The method of claim 12, wherein the applying an electric field comprises dielectric separation of the target components from contaminants.

14. The method of claim 5, further comprising:
applying a magnetic field to the microfluidic filter chip.

15. A method to detect at least one target component in a fluid comprising:
performing the method of claim 5; and
detecting the at least one target component.

16. The method of claim 15, wherein the detecting comprises measuring capacitance to detect different types of cells, measuring refractive index, introducing fluorescent labels and measuring fluorescence of fluorescently-labeled species, and/or introducing nanoparticle labels and detecting nanoparticle-labeled species with optical or electromagnetic measurements.

17. A method of point-of-care testing through the array according to claim 1, the method comprising:
isolating fluid from a patient;
providing the fluid to an input of the array; and
directing the target components to corresponding flow channels based on size of the target components, thus separating the fluid.

\* \* \* \* \*